United States Patent [19]

Piazza et al.

[11] Patent Number: 5,238,965
[45] Date of Patent: Aug. 24, 1993

[54] METHODS OF USING LYSOPHOSPHATIDIC ACIDS FOR REGULATING SKIN WRINKLES

[75] Inventors: Gary A. Piazza, West Chester; Adam W. Mazur, Cincinnati, both of Ohio

[73] Assignee: The Procter & Gamble Company, Cincinnati, Ohio

[21] Appl. No.: 708,270

[22] Filed: May 31, 1991

[51] Int. Cl.$^5$ .......................... A61K 7/40; A61K 7/48; A61K 9/10; A61K 9/12

[52] U.S. Cl. .................................... 514/844; 252/106; 252/107; 424/DIG. 5; 424/47; 424/59; 424/60; 424/63; 424/195.1; 514/167; 514/251; 514/458; 514/474; 514/773; 514/783; 514/846; 514/847; 514/873; 514/886; 514/887; 514/937; 514/938; 514/944; 514/960

[58] Field of Search .............................. 514/844, 847

[56] References Cited

U.S. PATENT DOCUMENTS 4,104,403  8/1978  Barker et al. .................. 424/365

FOREIGN PATENT DOCUMENTS 1-174355A  7/1989  Japan .

OTHER PUBLICATIONS

Chem. Abs., May 1990, vol. 113(14):120831v, Ota.
Chem. Abs., Mar. 1991, vol. 115(18):18949h, Uchida.
Chem. Abs., Mar. 1991, vol. 115(20):214536w, Ota.
Chem. Abs., May 1986, vol. 105(18):158623b, Kondo et al.
Chem. Abs., Aug. 1986, vol. 105(22):196975a, Kondo et al.
Chem. Abs., Aug. 1986, vol. 106(6):38235a, Kondo et al.
Chem. Abs., Aug. 1986, vol. 106(6)38238d, Kondo et al.
Chem. Abs., Aug. 1986, vol. 106(8), 55625v, Kondo et al.
Chem. Abs., Sep. 1986, vol. 106(10), 72706q, Kondo et al.
Chem. Abs., Jul. 1987, vol. 108(4), 26827y, Togiya et al.
Chem. Abs., Oct. 1987, vol. 108(14), 118734y, Togiya et al.
van Corven, E. J., A. Groenick, K. Jalink, T. Eichholtz & W. H. Moolenaar, "Lysophosphatidate-Induced Cell Proliferation: Identification and Dissection of Signaling Pathways Mediated by G Proteins", Cell, vol. 59 (Oct. 6, 1989), pp. 45-54.
Moolenaar, W. H. & E. J. van Corven, "Growth Factor-Like Action of Lysophosphatidic Acid: Mitogenic Signalling Mediated by G Proteins", 1990 Protooncogenes in Cell Development, Wiley, Chichester (Ciba Foundation Symposium 150) pp. 99-111.

Primary Examiner—Dale R. Ore
Attorney, Agent, or Firm—M. B. Graff; D. L. Suter; J. J. Yetter

[57] ABSTRACT

The subject invention relates to methods for regulating wrinkles in mammalian skin comprising topical application of a lysophosphatidic acid compound having the structure:

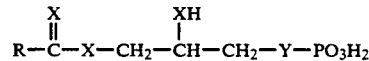

or a cyclic derivative thereof having the structure:

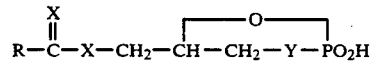

or a pharmaceutically acceptable salt thereof, wherein —R is unsubstituted or substituted, saturated or unsaturated, straight or branched chain alkyl having from 12 to about 23 carbon atoms; each —X— is independently —O— or —S—; and —Y— is —O— or —CH$_2$—.

16 Claims, No Drawings

METHODS OF USING LYSOPHOSPHATIDIC ACIDS FOR REGULATING SKIN WRINKLES

TECHNICAL FIELD

The present invention relates to the field of anti-aging of skin. Specifically, the invention relates to novel methods of using lysophosphatidic acid compounds for effacing and preventing wrinkles in mammalian skin.

BACKGROUND OF THE INVENTION

Skin is subject to abuse by many extrinsic (environmental) factors as well as intrinsic (aging) factors. A common extrinsic factor is exposure to ultraviolet radiation. Whether extrinsic or intrinsic, the abuse results in wrinkling of the skin. To many people, skin wrinkles are a reminder of the disappearance of youth. As a result, the elimination of wrinkles has become a booming business in youth-conscious societies. Treatments range from cosmetic creams and moisturizers to various forms of cosmetic surgery.

Lysophosphatidic acids are disclosed to be useful as emulsifiers for food products. U.S. Pat. No. 4,104,403 issued to Barker & Barabash on Aug. 1, 1978 discloses the use of lysophosphatidic acids as emulsifiers in cosmetics. Japanese Patent Application No. 1174-355-A of Asahi Denka Kogyo, published Jul. 10, 1989, discloses lysophosphatidic acids to be transdermal absorption potentiators. Certain lysophosphatidic acids are disclosed to have growth factor-like activity in van Corven, E.J., A. Groenink, K. Jalink, T. Eichholtz & W.H. Moolenaar, "Lysophosphatidate-Induced Cell Proliferation: Identification and Dissection of Signaling Pathways Mediated by G Proteins", *Cell*, Vol. 59 (Oct. 6, 1989), pp. 45-54; Moolenaar, W.H. & E.J. van Corven, "Growth Factor-Like Action of Lysophosphatidic Acid: Mitogenic Signalling Mediated by G Proteins", 1990 *Protooncogenes in Cell Development*, Wiley, Chichester (Ciba Foundation Symposium 150) pp. 99-111.

It is an object of the subject invention to provide methods of regulating skin wrinkles in mammalian skin by topically applying certain compounds to the skin.

SUMMARY OF THE INVENTION

The subject invention involves a method of regulating wrinkles comprising topically applying to the skin of a mammal a composition comprising a safe and effective amount of a lysophosphatidic acid compound or derivative having the structure:

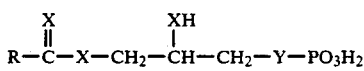

or a cyclic derivative thereof having the structure:

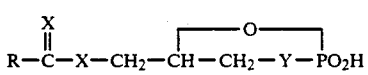

or a pharmaceutically acceptable salt thereof, wherein —R is unsubstituted or substituted, saturated or unsaturated, straight or branched chain alkyl having from 12 to about 23 carbon atoms; each —X— is independently —O— or —S—; and —Y— is —O— or —CH$_2$—.

DETAILED DESCRIPTION OF THE INVENTION

As used herein, "alkyl" means a substituted or unsubstituted carbon-containing chain which may be straight or branched; saturated, monounsaturated (i.e., one double or triple bond in the chain), or polyunsaturated (i.e., two or more double bonds in the chain; two or more triple bonds in the chain; one or more double and one or more triple bonds in the chain).

As used herein, "topical application" means directly laying on or spreading on outer skin.

As used herein, "pharmaceutically-acceptable" means that salts, drugs, medicaments or inert ingredients which the term describes are suitable for use in contact with the tissues of humans and lower animals without undue toxicity, incompatibility, instability, irritation, allergic response, and the like, commensurate with a reasonable benefit/risk ratio.

As used herein, "safe and effective amount" means an amount of compound or composition sufficient to significantly induce a positive modification in the condition to be treated, but low enough to avoid serious side effects (at a reasonable benefit/risk ratio), within the scope of sound medical judgment. The safe and effective amount of the compound or composition will vary with the particular condition being treated, the age and physical condition of the patient being treated, the severity of the condition, the duration of the treatment, the nature of concurrent therapy, the specific compound or composition employed, the particular pharmaceutically-acceptable carrier utilized, and like factors within the knowledge and expertise of the attending physician.

As used herein, "anti-wrinkle agent" means a lysophosphatidic acid, or a pharmaceutically-acceptable salt thereof, as defined hereinbelow.

As used herein, "regulating wrinkles" means preventing, retarding, arresting, or reversing the process of wrinkle formation in mammalian skin. Another manifestation often associated with regulating wrinkles is a smoother feel to the skin.

As used herein, all percentages are by weight unless otherwise specified.

Active Agent

The subject invention involves a method for regulating wrinkles in mammalian skin by topically applying to the skin a safe and effective amount of a lysophosphatidic acid compound or derivative having the structure:

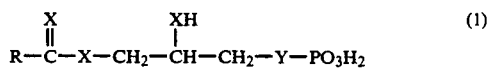

or a cyclic derivative thereof having the structure:

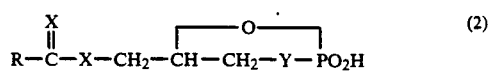

or a pharmaceutically-acceptable salt thereof, wherein —R is unsubstituted or substituted, saturated or unsaturated, straight or branched-chain alkyl having from 12 to about 23 carbon atoms; each —X— is independently —O— or —S—; and —Y— is —O— or —CH—.

Structure (1) above is preferred.

Preferred —X— is —O—.
Preferred —Y— is —O—.
Preferred —R is straight-chain.
Preferred —R has from about 13 to about 19 carbon atoms, more preferably from about 13 to about 17 carbon atoms.

Preferred —R is saturated or unsaturated with from one to about 3 double bonds, more preferably 1 or 2 double bonds, more preferably still one double bond; most preferred is —R being saturated.

Preferred —R is unsubstituted or substituted with halogen, hydroxy, phenyl, amino or acylamino; more preferred —R is unsubstituted or substituted with halogen or hydroxy; most preferred —R is unsubstituted.

Particularly preferred is RC(O)O— being myristyl, palmityl, stearyl, palmitoleyl, oleyl or linoleyl; especially oleyl, myristyl or palmityl.

Structures (1) and (2) above can be in either D or L configuration or can be a mixture of D and L.

Preferred pharmaceutically-acceptable salts of lysophosphatidic acid compounds include alkali metal salts, such as sodium and potassium; alkaline earth metal salts, such as calcium and magnesium; non-toxic heavy metal salts; ammonium salts; and trialkylammonium salts, such as trimethylammonium and triethylammonium.

Preferred compounds useful in the methods and compositions of the subject invention include L and D 1-oleoyl glycerol-3-phosphate (oleyl lysophosphatidic acid) L and D 1-myrystoyl glycerol-3-phosphate (myristyl lysophosphatidic acid), and L and D 1-palmitoyl glycerol-3-phosphate (palmityl lysophosphatidic acid), and salts thereof and mixtures thereof.

Example I provides a non-limiting example of the preparation of a lysophosphatidic acid compound useful in the subject invention.

EXAMPLE I

Preparation of 1-Oleoyl Glycerol-3-Phosphate

All glassware is oven dried. The reactions are run under nitrogen. To a solution of dibenzyl phosphite (78.8 mmole, 20.67 g) in CCl4 (300 ml) is slowly added sulfuryl chloride (74 mmol, 9.99 g) in CCl4 while the temperature is maintained at 16-19° C. When the addition is complete, nitrogen is bubbled vigorously through the reaction mixture for 90 minutes and the solvent is evaporated. The oily residue is dissolved in CCl4 and slowly added to a solution of 1,2-isopropylidene-sn-glycerol (Aldrich Chem. Co., 45 mmol, 6.0 g) in dry pyridine (15 ml) at 0° C. The reaction mixture is allowed to reach room temperature and is stirred for 1 hour. The precipitate of pyridinium chloride is filtered. The filtrate is diluted with chloroform (200 ml). The organic solution is extracted with 1N HCl (2×100 ml), aqueous sodium bicarbonate (100 ml) and water (100 ml). The organic layer is dried with anhydrous sodium sulfate and evaporated. The residue is chromatographed on a silica column using a solution of 50:50:1 hexanes:ethyl ether:acetic acid. The product is 1,2-isopropylidene-3-(O,O-dibenzylphosphate)-snglycerol (1).

Hydrolysis of the isopropylidene group in compound (1) is accomplished by mixing the substrate (5 g) with a solution of tetrahydrofuran (100 ml), 1N HCl (100 ml), and methanol (5 ml) at room temperature for 2.5 hours. After neutralization with 1 N NaOH, the solvents are evaporated and the product is purified on a silica column. The product is 3-(O,O-dibenzylphosphate)-sn-glycerol (2).

A solution of oleic anhydride (11.4 mmol, 6.2 g) and 4-N,N-dimethylaminopyridine (DMAP) (0.57 mmol, 0.07 g) in dry methylene chloride (50 ml) is added to compound (2) (11.4 mmol, 4.0 g) in methylene chloride (100 ml) at 0° C. over a period of 2 hours. After mixing for an additional 2 hours at room temperature, the reaction mixture is washed with 1N HCl (100 ml) and evaporated. The crude product is purified on a silica column using for elution a solution of hexane:ethyl ether:acetic acid 50:50:1 (1000 ml), followed by a solution of hexane:ethyl ether:acetic acid 40:60:1. The product is 3-(O,O-dibenzylphosphate)-sn-1-oleoylglycerol (3).

It is important in the next step that reagents and vessels be absolutely dry, bromotrimethylsilane be of high purity (free from HBr and Br2), and the reaction be run in an inert gas atmosphere. Compound (3) (4.86 mmol, 3.0 g) is dissolved in dry, alcohol-free chloroform (25 ml). N,O-bis(trimethylsilyl) trifluoroacetamide (Pierce Chem. Co., 14.6 mmol, 3.75 ml) is added followed by bromotrimethylsilane ( Aldrich Chem. Co., 9.8 mmol, 1.3 ml). The reaction is complete after 5-10 minutes. The solvents are immediately evaporated. The residue is dissolved in acetone (9.5 ml) and treated with water (0.5 ml). The solvents are evaporated. The product is purified by silica gel chromatography using 4:1 chloroform methanol. The product is 1'-oleoyl glycerol-3-phosphate.

EXAMPLE II

Preparation of 1-O-Hexadecanoyl-1,2-Cyclic-sn-Glycerolphosphate

To a solution of 1-hexadecanoyl-sn-glycerol (Sigma Chem. Co., 0.76 mmol, 250 mg) in dry pyridine (5 ml) is added phosphorus oxychloride (1.13 mmol, 250 mg) at 0° C. After stirring at this temperature for 30 minutes, 1M sodium acetate (20 ml) is added and the mixture is kept overnight at 5° C. The precipitated product is filtered and dried over P2O5. The product is 1-O-hexadecanoyl-1,2-cyclic-sn-glycerolphosphate in the form of its sodium salt:

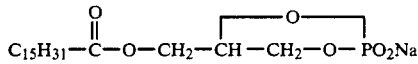

EXAMPLE III

Preparation of 3-Hydroxy-4-tetradecanoyloxyphosphonic Acid 1,2-Isopropylidene-glyceraldehyde prepared from 1,2-5,6-diisopropylidene mannitol (7.5 g) (Baer, E. & H.O.L. Fisher, *J. Biol. Chem.*, Vol. 128 (1939), pp. 463-473), is reacted with butyllithium (27.8 mmol, 11.1 ml) and tetraisopropyl methylenediphosphonate (27.6 mmol, 7.41 g) in heptane (150 ml) (Gupta, A., K. Sacks, S. Khan, B.E. Tropp & R. Engel, "An Improved Synthesis of Vinylic Phosphonates from Ketones", *Synthetic Communications*, Vol. 10, No. 4 (1980), pp. 299-304. The product is purified on a silica gel column to yield the unsaturated compound diisopropyl 3,4-dihydroxybuten-1-ylphosphonate, HOCH2—CHOH—CH=CH—P(O)— (OCH(CH3)2)2, which is hydrogenated at atmospheric pressure using 10% Pd(OH)2 on charcoal (1.0 g) in 95% MeOH (100 ml).

The product is diisopropyl 3,4-dihydroxybutylphosphonate (4).

Compound (4) (500 mg) is stirred with myristic acid anhydride (2.17 g) and lipozyme (2 g) in methylene chloride (50 ml) at room temperature for 2 hours. The enzyme is removed by filtration. The filtrate is evaporated and the product, 3-hydroxy-4-tetradecanoyloxybutylphosphonate (5), is purified on a silica column using 50:50:1 hexane:ethyl acetate:acetic acid. Compound (5) (0.432 mmol, 0.2 g) is dissolved in dry, alcoholfree chloroform (2 ml). N-0-bis(trimethylsilyl)trifluoroacetamide (0.9 mmol, 0.2 ml) is added, followed by addition of bromotrimethylsilane (1.3 mmol, 0.17 ml) from a syringe over a period of 1 hour. The reaction is complete after 6 hours. The solvents are evaporated. The residue is dissolved in acetone (2 ml) and treated with water (0.2 ml). The product, 3-hydroxy-4-tetradecanoyloxyphosphonic acid, crystallizes upon cooling. The methods of the subject invention preferably involve topical application of a composition to mammalian skin, the composition comprising an active anti-wrinkle agent or mixture of active anti-wrinkle agents as described hereinabove and a pharmaceutically-acceptable topical carrier.

The term "pharmaceutically-acceptable topical carrier", as used herein, means one or more compatible solid or liquid filler diluents which are suitable for topical administration to a human or lower animal. Pharmaceutically-acceptable topical carriers must be of sufficiently high purity and sufficiently low toxicity to render them suitable for topical administration to the human or lower animal being treated. A safe and effective amount of carrier is preferably from about 50% to about 99.99%, more preferably from about 90% to about 99% of the composition.

Variations in formulation of these carriers will result in a wide variety of products which fall within the scope of the subject invention.

Topical Compositions

The topical compositions useful in the subject invention may be made into a wide variety of product types. These include, but are not limited to lotions, creams, beach oils, gels, sticks, sprays, ointments, pastes, mousses and cosmetics. These product types may comprise several types of carrier systems including, but not limited to solutions, emulsions, gels and solids.

The topical compositions useful in the subject invention formulated as solutions typically include a pharmaceuticallyacceptable aqueous or organic solvent. The terms "pharmaceutically-acceptable aqueous solvent" and "pharmaceuticallyacceptable organic solvent" refer to a solvent which is capable of having dispersed or dissolved therein the anti-wrinkle agent, and possesses acceptable safety properties (e.g., irritation and sensitization characteristics). Water is a preferred solvent. Examples of suitable organic solvents include: propylene glycol, polyethylene glycol (200-600), polypropylene glycol (425-2025), glycerol, 1,2,4-butanetriol, sorbitol esters, 1,2,6-hexanetriol, ethanol, isopropanol, butanediol, and mixtures thereof. These solutions useful in the subject invention preferably contain from about .01% to about 20%, more preferably from about 0.1% to about 10% of the anti-wrinkle agent, and preferably from about 80% to about 99.99%, more preferably from about 90% to about 99.9% of an acceptable aqueous or organic solvent.

Aqueous containing topical compositions of the subject invention preferably contain a calcium chelator to prevent precipitation of insoluble salts of lysophosphatidic acid compounds. Preferred calcium chelators include ethylenediaminetetraacetic acid (EDTA) and ethylene glycol bis($\beta$-aminoethyl ether)-N,N,N',N'-tetraacetic acid (EGTA).

If the topical compositions useful in the subject invention are formulated as an aerosol and applied to the skin as a sprayon, a propellant is added to a solution composition. Examples of propellants useful herein include, but are not limited to, the chlorinated, fluorinated and chloro-fluorinated lower molecular weight hydrocarbons. A more complete disclosure of propellants useful herein can be found in Sagarin, *Cosmetics Science and Technology*, 2nd Edition, Vol. 2, pp. 443-465 (1972).

Topical compositions useful in the subject invention may be formulated as a solution comprising an emollient. An example of a composition formulated in this way would be a beach oil product. Such compositions preferably contain from about .01% to about 20% of the anti-wrinkle agent and from about 2% to about 50% of a topical pharmaceutically-acceptable emollient.

As used herein, "emollients" refer to materials used for the prevention or relief of dryness, as well as for the protection of the skin. A wide variety of suitable emollients are known and may be used herein. Sagarin, *Cosmetics, Science and Technology*, 2nd Edition, Vol. 1, pp. 32-43 (1972), incorporated herein by reference, contains numerous examples of suitable materials.

A lotion can be made from a solution carrier system. Lotions typically comprise from about 0.01% to about 20%, preferably from about 0.1% to about 10%, of the anti-wrinkle agent; from about 1% to about 20%, preferably from about 5% to about 10%, of an emollient; and from about 50% to about 90%, preferably from about 60% to about 80%, water.

Another type of product that may be formulated from a solution carrier system is a cream. A cream typically comprises from about 0.01% to about 20%, preferably from about 0.1% to about 10%, of the anti-wrinkle agent; from about 5% to about 50%, preferably from about 10% to about 20%, of an emollient, and from about 45% to about 85%, preferably from about 50% to about 75%, water.

Yet another type of product that may be formulated from a solution carrier system is an ointment. An ointment may comprise a simple base of animal or vegetable oils or semi-solid hydrocarbons (oleaginous). Ointments may also comprise absorption ointment bases which absorb water to form emulsions. Ointment carriers may also be water soluble. An ointment may also comprise from about 2% to about 10% of an emollient plus from about 0.1% to about 2% of a thickening agent. A more complete disclosure of thickening agents useful herein can be found in Segarin, *Cosmetics, Science and Technology*, 2nd Edition, Vol. 1, pp. 72-73 (1972).

If the carrier is formulated as an emulsion, preferably from about 1% to about 10%, more preferably from about 2% to about 5%, of the carrier system comprises an emulsifier. Emulsifiers may be nonionic, anionic or cationic. Suitable emulsifiers are disclosed in, for example, U.S. Pat. No. 3,755,560, issued Aug. 28, 1973, Dickert et al,,; U.S. Pat. No. 4,421,769, issued Dec. 20, 1983, Dixon et al.; and McCutcheon's *Detergents and Emulsifiers*, North American Edition, pages 317-324 (1986); the disclosures of which are incorporated herein by reference. Preferred emulsifiers are anionic or nonionic, although the other types may also be used.

Lotions and creams can be formulated as emulsions as well as solutions. Typically such lotions comprise from about .01% to about 20%, preferably from about 0.1% to about 10%, of the anti-wrinkle agent; from about 1% to about 20%, preferably from about 5% to about 10%, of an emollient; from about 25% to about 75%, preferably from about 45% to about 95%, water; and from about 0.1% to about 10%, preferably from about 0.5% to about 5%, of an emulsifier. Such creams would typically comprise from about .01% to about 20%, preferably from about 0.1% to about 10%, of the anti-wrinkle agent; from about 1% to about 20%, preferably from about 5% to about 10%, of an emollient; from about 20% to about 80%, preferably from about 30% to about 70%, water; and from about 1% to about 10%, preferably from about 2% to about 5%, of an emulsifier.

Single emulsion skin care preparations, such as lotions and creams, of the oil-in-water type and water-in-oil type are wellknown in the cosmetic art and are useful in the subject invention. Multiphase emulsion compositions, such as the waterin-oil-in-water type, as disclosed in U.S. Pat. No. 4,254,105, Fakuda et al., issued Mar. 3, 1981, incorporated herein by reference, are also useful in the subject invention. In general, such single or multiphase emulsions contain water, emollients and emulsifiers as essential ingredients.

Triple emulsion carrier systems comprising an oil-in-waterin-silicone fluid emulsion composition as disclosed in U.S. Pat. No. 4,960,764, Figueroa, issued Oct. 2, 1990, are also useful in the subject invention. This triple emulsion carrier system is preferably combined with from about 0.01% to about 20%, more preferably from about 0.1% to about 10%, of the anti-wrinkle agent to yield a topical composition useful in the subject invention.

Another emulsion carrier system useful in the topical compositions is a micro-emulsion carrier system. Such a system comprises from about 9% to about 15% squalane; from about 25% to about 40% silicone oil; from about 8% to about 20% of a fatty alcohol; from about 15% to about 30% of polyoxyethylene sorbitan monofatty acid (commercially available under the trade name Tweens) or other nonionics; and from about 7% to about 20% water. This carrier system is preferably combined with from about 0.1% to about 10% of the anti-wrinkle agent.

Liposomal formulations are also useful compositions of the subject invention. Such compositions can be prepared by first combining an anti-wrinkle agent with a phospholipid, such as dipalmitoylphosphatidyl choline, cholesterol and water according to the method described in Mezei & Gulasekharam, "Liposomes - A Selective Drug Delivery System for the Topical Route of Administration: Gel Dosage Form", *Journal of Pharmaceutics and Pharmacology*, Vol 34 (1982), pp. 473-474, incorporated herein by reference, or a modification thereof. Epidermal lipids of suitable composition for forming liposomes may be substituted for the phospholipid. The liposome preparation is then incorporated into one of the above topical carrier systems (for example, a gel or an oil-in-water emulsion) in order to produce the liposomal formulation. The final formulation preferably contains from about 0.01% to about 10%, more preferably from about 0.1% to about 5%, of the anti-wrinkle agent. Other compositions and pharmaceutical uses of topically applied liposomes are described in Mezei, M., "Liposomes as a Skin Drug Delivery System", *Topics in Pharmaceutical Sciences* (D.D. Breimer and P. Speiser, eds.), Elsevier Science Publishers B.V., New York, NY, 1985, pp. 345-358, incorporated herein by reference.

If the topical compositions useful in the subject invention are formulated as a gel or a cosmetic stick, such compositions can be formulated by the addition of a suitable amount of a thickening agent, as disclosed suora. to a cream or lotion formulation.

Topical compositions useful in the subject invention may also be formulated as makeup products, such as foundations.

The topical compositions useful in the subject invention may contain, in addition to the aforementioned components, a wide variety of additional oil-soluble materials and/or water-soluble materials conventionally used in topical compositions, at their art-established levels.

Various water-soluble materials may also be present in the compositions useful in the subject invention. These include humectants, proteins and polypeptides, preservatives and an alkaline agent. In addition, the topical compositions useful herein can contain conventional cosmetic adjuvants, such as dyes, spacifiers (e.g., titanium dioxide), pigments and perfumes.

The topical compositions useful in the subject invention may also include a safe and effective amount of a penetration enhancing agent. A preferred amount of penetration enhancing agent is from about 1% to about 5% of the composition. Examples of useful penetration enhancers, among others, are disclosed in U.S. Pat. Nos. 4,537,776, Cooper, issued Aug. 27, 1985; 4,552,872, Cooper et al., issued Nov. 12, 1985; 4,557,934, Cooper, issued Dec. 10, 1985; 4,130,667, Smith, issued Dec. 19, 1978; 3,989,816, Rhaadhyaksha, issued Nov. 2, 1976; 4,017,641, DiGiulio, issued Apr. 12, 1977; and 4,954,487, Cooper, Loomans & Wickett, issued Sep. 4, 1990. Additional penetration enhancers useful in the subject invention are disclosed in Cooper, E.R., "Effect of Decylmethylsulfoxide on Skin Penetration", *Solution Behavior of Surfactants*, Vol. 2 (Mittal and Fendler, eds.), Plenum Publishing Corp., 1982, pp. 1505-1516; Mahjour, M., B. Mauser, Z. Rashidbaigi & M.B. Fawzi, "Effect of Egg Yolk Lecithins and Commercial Soybean Lecithins on In Vitro Skin Permeation of Drugs", *Journal of Controlled Release*, Vol. 14 (1990), pp. 243-252; Wong, O., J. Huntington, R. Konishi, J.H. Rytting & T. Higuchi, "Unsaturated Cyclic Ureas as New Nontoxic Biodegradable Transdermal Penetration Enhancers I: Synthesis", *Journal of Pharmaceutical Sciences*, Vol. 77, No. 11 (Nov. 1988), pp. 967-971; Williams, A.C. & B.W. Barry, "Terpenes and the Lipid-Protein-Partitioning Theory of Skin Penetration Enhancement", *Pharmaceutical Research*, Vol. 8, No. 1 (1991), pp. 17-24; and Wong, O., J. Huntington, T. Nishihata & J.H. Rytting, "New Alkyl N,N-Dialkyl-Substituted Amino Acetates as Transdermal Penetration Enhancers", *Pharmaceutical Research*, Vol. 6, No. 4 (1989), pp. 286-295. The above references are incorporated herein by reference.

Other conventional skin care product additives may also be included in the compositions useful in the subject invention. For example, collagen, hyaluronic acid, elastin, hydrolysates, primrose oil, jojoba oil, epidermal growth factor, soybean saponins, mucopolysaccharides, and mixtures thereof may be used.

Various vitamins may also be included in the compositions useful in the subject invention. For example, Vitamin A, and derivatives thereof, Vitamin B, biotin, pantothenic, Vitamin D, and mixtures thereof may be used.

Cleaning Compositions

Skin cleaning compositions useful in the subject invention comprise, in addition to the anti-wrinkle agent, a cosmeticallyacceptable surfactant. The term "cosmetically-acceptable surfactant" refers to a surfactant which is not only an effective skin cleanser, but also can be used without undue toxicity, irritation, allergic response, and the like. Furthermore, the surfactant must be capable of being commingled with the antiwrinkle agent in a manner such that there is no interaction which would substantially reduce the efficacy of the composition for effacing or preventing skin wrinkles.

The skin cleaning compositions useful in the subject invention preferably contain from about 0.01% to about 20%, more preferably from about 0.1% to about 10%, of the anti-wrinkle agent and preferably from about 1% to about 90%, more preferably from about 5% to about 10%, of a cosmetically-acceptable surfactant.

The physical form of the skin cleansing compositions is not critical. The compositions can be, for example, formulated as toilet bars, liquids, pastes, or mousses. Toilet bars are most preferred since this is the form of cleansing agent most commonly used to wash the skin.

The surfactant component of the compositions useful in the subject invention are selected from anionic, nonionic, zwitterionic, amphoteric and ampholytic surfactants, as well as mixtures of these surfactants. Such surfactants are well-known to those skilled in the detergency art.

The cleaning compositions useful in the subject invention can optionally contain, at their art-established levels, materials which are conventionally used in skin cleansing compositions.

Combination Actives

A. Sunscreens and Sunblocks

Regulation of skin wrinkling resulting from exposure to ultraviolet light can be achieved by using combinations of the anti-wrinkle agents together with sunscreens or sunblocks. Useful sunblocks include, for example, zinc oxide and titanium dioxide.

Photo damage by ultraviolet light is a predominant cause of skin wrinkling. Thus, for purposes of wrinkle prevention, the combination of an anti-wrinkle agent with a UVA and/or UVB sunscreen is desirable. The inclusion of sunscreens in compositions useful in the subject invention at low levels does not greatly reduce the tanning response of the user but enhances immediate protection against acute UV damage.

A wide variety of conventional sunscreening agents are suitable for use in combination with the anti-wrinkle agent. Segarin, et al., at Chapter VIII, pages 189 et seq., of *Cosmetics Science and Technology*, disclose numerous suitable agents. Specific suitable sunscreening agents include, for example: p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, benzyl, menthyl, glyceryl, and dipropyleneglycol esters); Cinnamic acid derivatives (menthyl and benzyl esters, o-phenyl cinnamonitrile; butyl cinnamoyl pyruvate); dihydroxycinnamic acid derivatives (umbelliferone, methylumbelliferone, methylaceto-umbelliferone); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); dihydroxy-naphthoic acid and its salts; o- and p-Hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and vilouric acids; tannic acid and its derivatives (e.g., hexaethylether); (butyl carbotol) (6-propyl piperonyl) ether; hydroquinone; benzophenones (oxy, benzene sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; and 4-isopropyl-di-benzoylmethane.

Of these, 2-ethylhexyl-p-methoxycinnamate, 4,4'-t-butyl methoxydibenzoylmethane, 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexylsalicylate, glyceryl-p-aminobenzoate, 3,3,5-trimethylcyclohexylsalicylate, methylanthranilate, p-dimethylaminobenzoic acid or aminobenzoate, 2-ethylhexyl-p-dimethylamino-benzoate, 2-phenylbenzimidazole-5-sulfonic acid, 2-(p-dimethylaminophenyl)-5-sulfonicbenzoxazoic acid and mixtures of these compounds, are preferred.

More preferred sunscreens useful in the compositions useful in the subject invention are 2-ethylhexyl-p-methoxycinnamate, butylmethoxydibenzoylmethane, 2-hydroxy-4-methoxybenzophenone, octyldimethyl-p-aminobenzoic acid and mixtures thereof.

Also particularly useful in the compositions are sunscreens such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991, both of which are incorporated herein by reference. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methylaminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl) methylaminobenzoic acid ester with 4-hydroxydibenzoylmethane; 4-N,N-(2-ethylhexyl)methylaminobenzoic acid ester of 2-hydroxy4-(2-hydroxyethoxy)benzophenone; 4-N,N-(2-ethylhexyl)-methylaminobenzoic acid ester of 4-(2-hydroxyethoxy)dibenzoylmethane; N,N-di-(2-ethylhexyl)-4-aminobenzoic acid ester of 2-hydroxy-4-(2-hydroxyethoxy)benzophenone; and N,N-di-(2-ethlhexyl)-4-aminobenzoic acid ester of 4-(2-hydroxyethoxy)dibenzoylmethane and mixtures thereof.

A safe and effective amount of sunscreen may be used in the anti-wrinkle agent compositions useful in the subject invention. The sunscreening agent must be compatible with the anti-wrinkle agent. The composition preferably comprises from about 1% to about 20%, more preferably from about 2% to about 10%, of a sunscreening agent. Exact amounts will vary depending upon the sunscreen chosen and the desired Sun Protection Factor (SPF).

An agent may also be added to any of the compositions useful in the subject invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

B. Anti-Inflammatory Agents

In a preferred wrinkle regulating composition useful in the subject invention, an anti-inflammatory agent is included as an active along with the anti-wrinkle agent. The inclusion of an anti-inflammatory agent enhances the wrinkle regulating benefits of the compositions. The anti-inflammatory agent protects strongly in the UVA radiation range (though it also provides some UVB protection as well). The topical use of anti-inflammatory agents reduces photo-aging of the skin resulting from chronic exposure to UV radiation. (See U.S. Pat. No. 4,847,071, Bissett, Bush, and Chatterjee, issued Jul. 11, 1989, incorporated herein by reference; and U.S. Pat. No. 4,847,069, Bissett and Chatterjee, issued Jul. 11, 1989, incorporated herein by reference.)

A safe and effective amount of an anti-inflammatory agent may be added to the compositions useful in the subject invention, preferably from about 0.1% to about 10%, more preferably from about 0.5% to about 5%, of the composition. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasonephosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

A second class of anti-inflammatory agents which is useful in the compositions includes the nonsteroidal anti-inflammatory agents. The variety of compounds encompassed by this group are well-known to those skilled in the art. For detailed disclosure of the chemical structure, synthesis, side effects, etc., of non-steroidal anti-inflammatory agents, reference may be had to standard texts, including *Antiinflammatory and Anti-Rheumatic Drugs*, K. D Rainsford, Vol. 1-III, CRC Press, Boca Raton, (1985), and *Anti-inflammatory Agents, Chemistry and Pharmacology*, 1, R. A. Scherrer, et al., Academic Press, New York (1974).

Specific non-steroidal anti-inflammatory agents useful in the composition invention include, but are not limited to:

1) the oxicams, such as piroxicam, isoxicam, tenoxicam, sudoxicam, and CP-14,304;
2) the salicylates, such as aspirin, disalcid, benorylate, trilisate, safapryn, solprin, diflunisal, and fendosal;
3) the acetic acid derivatives, such as diclofenac, fenclofenac, indomethacin, sulindac, tolmetin, isoxepac, furofenac, tiopinac, zidometacin, acemetacin, fentiazac, zomepiract, clidanac, oxepinac, and felbinac;
4) the fenamates, such as mefenamic, meclofenamic, flufenamic, niflumic, and tolfenamic acids;
5) the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and
6) the pyrazoles, such as phenybutazone, oxyphenbutazone, feprazone, azapropazone, and trimethazone.

Mixtures of these non-steroidal anti-inflammatory agents may also be employed, as well as the pharmaceutically-acceptable salts and esters of these agents. For example, etofenamate, a flufenamic acid derivative, is particularly useful for topical application. Of the nonsteroidal anti-inflammatory agents, ibuprofen, naproxen, flufenamic acid, mefenamic acid, meclofenamic acid, piroxicam and felbinac are preferred; ibuprofen, naproxen, and flufenamic acid are most preferred.

Another class of anti-inflammatory agents which are useful in the compositions are the anti-inflammatory agents disclosed in U.S. Pat. No. 4,708,966, Loomans et al., issued Nov. 24, 1987. This patent discloses a class of nonsteroidal antiinflammatory compounds which comprise specifically substituted phenyl compounds, especially substituted 2,6-di- tert-butyl phenol derivatives. For example, compounds selected from 4-(4'-pentyn-3'-one)-2,6-di-t-butylphenol; 4-(5'-hexynoyl)-2,6-di-t-butylphenol; 4-((S)-(-)-3'-methyl-5'-hexynoyl)-2,6-di-t-butylphenol; 4-((R)-(+)-3 -methyl-5'-hexynoyl)-2,6-di-t-butylphenol; and 4-(3', 3'-dimethoxypropionyl)-2,6-di-t-butylphenol are useful in methods of the subject invention; 4-(5'-hexynoyl)-2,6-d-tbutylphenol is most preferred.

Yet another class of anti-inflammatory agents which are useful in the compositions are those disclosed in U.S. Pat. No. 4,912,248, Mueller, issued Mar. 27, 1990. This patent discloses compounds and diastereomeric mixtures of specific 2-naphthylcontaining ester compounds, especially naproxen ester and naproxol ester compounds, having two or more chiral centers. For example, compounds selected from (S)-naproxen-(S)-2-butyl ester, (S)-naproxen-(R)-2-butylester, (S)-naproxol-(R)-2-methyl butyrate, (S)-naproxol-(S)-2-methyl butyrate, diasteromeric mixtures of (S)-naproxen-(S)-2-butyl ester and (S)-naproxen(R)-2-butyl ester, and diasteromeric mixtures of (S)-naproxol(R)-2-methyl butyrate and (S)-naproxol-(S)-2-methyl butyrate are useful in the subject invention.

Finally, so-called "natural" anti-inflammatory agents are useful in methods of the subject invention. For example, candelilla wax, alpha bisabolol, aloe vera, Manjistha (extracted from plants in the genus Rubia, particularly *Rubia Cordifolial*, and Guggal (extracted from plants in the genus Commiohora, particularly *Commiohora Mukul*), may be used.

Another preferred composition useful in the subject invention comprises an anti-wrinkle agent, a sunscreen, and an anti-inflammatory agent together for wrinkle regulation in the amounts disclosed for each individually hereinabove.

C. Anti-Oxidants/Radical Scavengers

In a preferred wrinkle regulating composition useful in the subject invention, an anti-oxidant/radical scavenger is included as an active along with the anti-wrinkle agent. The inclusion of an anti-oxidant/radical scavenger increases the wrinkle regulating benefits of the composition.

A safe and effective amount of an anti-oxidant/radical scavenger may be added to the compositions useful in the subject invention, preferably from about 0.1% to about 10%, more preferably from about 1% to about 5%, of the composition.

Anti-oxidants/radical scavengers such as ascorbic acid (vitamin C) and its salts, tocopherol (vitamin E), tocopherol sorbate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, the ascorbyl esters of fatty acids, amines (e.g., N,N-diethylhydroxylamine, amino-guanidine), sulfhydryl compounds (e.g., glutathione), and dihydroxy fumaric acid and its salts may be used.

In a preferred wrinkle regulating composition useful in the subject invention, compositions comprise one, any two, or all three of a sunscreening agent, anti-inflammatory agent, and/or an anti-oxidant/radical scavenging agent included as actives along with the anti-wrinkle agent. The inclusion of two or all three of these agents with the anti-wrinkle agent increases the wrinkle regulating benefits of the composition.

D. Chelators

In a preferred wrinkle regulating composition useful in the subject invention, a chelating agent is included as an active along with the anti-wrinkle agent. As used herein, "chelating agent" means an active agent capable of removing a metal ion from a system by forming a complex so that the metal ion cannot readily participate in or catalyze chemical reactions. The inclusion of a chelating agent increases the wrinkle regulating benefits of the composition.

A safe and effective amount of a chelating agent may be added to the compositions useful in the subject invention, preferably from about 0.1% to about 10%, more preferably from about 1% to about 5%, of the composition. Chelators useful in compositions are disclosed in U.S. patent application Ser. No. 619,805, Bissett, Bush & ChatterJee, filed Nov. 27, 1990 (which is a continuation of U.S. patent application Ser. No. 251,910, filed Oct. 4, 1988now abandoned); U.S. patent application Ser. No. 514,892, Bush & Bissett, filed Apr. 26, 1990; now abandoned; and U.S. patent application Ser. No. 657,847, Bush, Bissett & Chatterjee, filed Feb. 25, 1991, now abandoned; all incorporated herein by reference. Preferred chelators useful in compositions of the subject invention are furildioxime and derivatives thereof.

In a preferred wrinkle regulating composition useful in the subject invention, compositions comprise one, any two, any three, or all four of a sunscreening agent, anti-inflammatory agent, anti-oxidant/radical scavenging agent, and/or chelating agent included as actives along with the anti-wrinkle agent. The inclusion of two, three, or all four of these agents with the anti-wrinkle agent increases the wrinkle regulating benefits of the composition.

E. Retinoids

In a preferred wrinkle regulating composition useful in the subject invention, a retinoid, preferably retinoic acid, is included as an active along with the anti-wrinkle agent. The inclusion of a retinoid increases the wrinkle regulating benefits of the composition. A safe and effective amount of a retinoid may be added to the compositions useful in the subject invention, preferably from about 0.001% to about 2%, more preferably from about 0.01% to about 1% of the composition. As used herein, "retinoid" includes all natural and/or synthetic analogs of Vitamin A or retinol-like compounds which possess the biological activity of Vitamin A in the skin as well as the geometric isomers and stereoisomers of these compounds, such as all-trans retinoic acid and 13-cis-retinoic acid.

In a preferred wrinkle regulating composition useful in the subject invention, compositions comprise one, any two, any three, any four, and/or all five of a sunscreening agent, anti-inflammatory agent, anti-oxidant/radical scavenging agent, chelating agent, and/or a retinoid included as actives along with the anti-wrinkle agent. The inclusion of two, three, four, or all five of these agents with the anti-wrinkle agent increases the wrinkle regulating benefits of the composition.

Methods for Regulating Wrinkles in Mammalian Skin

The subject invention relates to methods for regulating wrinkles in mammalian skin. Such methods comprise topical application of a safe and effective amount of an anti-wrinkle agent. The amount of anti-wrinkle agent and frequency of application will vary widely depending upon the level of wrinkling already in existence in the subject, the rate of further wrinkle formation, and the level of regulation desired. Preferred regulation of wrinkling involves preventing or retarding the formation of wrinkles. More preferred regulation of wrinkling involves effacement of existing wrinkles.

A safe and effective amount of anti-wrinkle agent in a topical composition is applied, generally from about 0.001 mg to about 2 mg per cm$^2$ skin per application, preferably from about 0.01 mg to about 1 mg per cm$^2$ skin per application. Application preferably ranges from about monthly to about 5 times daily, more preferably from about biweekly to about daily, more preferably still from about weekly to about 3 times per week.

A preferred method of the subject invention for regulating wrinkles in mammalian skin involves applying both a safe and effective amount of the anti-wrinkle agent and a safe and effective amount of one or more of a sunscreening agent, an antiinflammatory agent, an anti-oxidant/radical scavenging agent, a chelating agent and/or a retinoid to the skin simultaneously. As used herein, "simultaneous application" or "simultaneously" means applying the agents to the skin at the same situs on the body at about the same time. Though this can be accomplished by applying the agents separately to the skin, preferably a composition comprising all the desired agents commingled is applied to the skin. The amount of sunscreening agent applied is preferably from about 0.05 mg to about 0.5 mg per cm$^2$ skin. The amount of anti-inflammatory agent applied is preferably from about 0.005 mg to about 0.5 mg, more preferably from about 0.01 mg to about 0.1 mg per cm$^2$ skin. The amount of anti-oxidant/radical scavenging agent preferably applied is from about 0.01 mg to about 1.0 mg, more preferably from about 0.05 mg to about 0.5 mg per cm$^2$ skin. The amount of chelating agent preferably applied is from about 0.001 mg to about 1.0 mg, more preferably from about 0.01 mg to about 0.5 mg, still more preferably from about 0.05 mg to about 0.1 mg per cm$^2$ skin. The amount of retinoid applied is preferably from about 0.001 mg to about 0.5 mg per cm$^2$ skin, more preferably from about 0.005 mg to about 0.1 mg per cm$^2$ skin. The amount of anti-wrinkle agent applied is preferably from about 0.001 mg to about 2 mg per cm$^2$ skin per application, more preferably from about 0.01 mg to about 1 mg per cm$^2$ skin per application.

The following examples further describe and demonstrate the preferred embodiments within the scope of the subject invention. The examples are given solely for the purpose of illustration, and are not to be construed as limitations of the subject invention since many variations thereof are possible without departing from its spirit and scope.

EXAMPLE IV

A simple topical composition is prepared by combining the following components utilizing conventional mixing techniques.

| Component | Percent by Weight Of Composition |
|---|---|
| Ethanol | 99.87 |
| Oleyl lysophosphatidic acid | 0.13 |

This composition is useful for topical application to regulate skin wrinkles. Use of an amount of the composition to deposit about 0.02 mg/cm$^2$ of the anti-wrinkle agent to the skin is appropriate.

EXAMPLE V

A nonionic oil-in-water emulsion is prepared by combining the following components utilizing conventional mixing techniques:

| Component | Percent by Weight Of Composition |
|---|---|
| Deionized Water | 79.73 |
| Propylene Glycol | 3.00 |
| Octyl Methoxycinnamate | 7.50 |
| Cetyl Alcohol | 2.50 |
| Stearyl Alcohol | 2.50 |
| Laureth 23 | 2.00 |
| C$_{12}$-C$_{15}$ Alcohols Benzoate | 2.00 |
| EDTA | 0.37 |
| Methylparaben | 0.20 |
| Propylparaben | 0.10 |
| Myristyl Lysophosphatidic Acid | 0.10 |

This composition is useful for topical application to regulate skin wrinkles. Use of an amount of the composition sufficient to deposit about 0.05 mg/cm$^2$ of the anti-wrinkle agent to the skin is appropriate.

EXAMPLE VI

An ion pair oil-in-water emulsion is prepared by combining the following components utilizing conventional mixing techniques.

| Component | Percent by Weight of Composition |
|---|---|
| Deionized Water | 78.05 |
| Permulon TR-2 (C10–C30 Acrylate Copolymer, B. F. Goodrich) | 0.30 |
| Distearyl Dimethyl Ammonium Chloride | 0.15 |
| Palmityl Lysophosphatidic Acid | 1.00 |
| 4-N,N-(2-ethylhexyl)methylaminobenzoic acid 4-ester of 2-hydroxy-4-(2-hydroxyethoxy)-benzophenone | 4.00 |
| 4-N,N-(2-ethylhexyl)methylaminobenzoic acid ester of 4-(2-hydroxyethoxy) dibenzoylmethane | 2.00 |
| Dimethyl Isosorbide | 6.00 |
| Dioctyl Malate | 6.00 |
| Cetyl Alcohol | 1.00 |
| Stearyl Alcohol | 1.00 |
| 99% Triethanolamine | 0.50 |

This composition is useful for topical application to inhibit damage caused by acute or chronic UV exposure. Use of an amount of the composition sufficient to deposit about 0.2 mg/cm$^2$ of the anti-wrinkle agent to the skin is appropriate.

EXAMPLE VII

A sunscreen composition is prepared by combining the following components utilizing conventional mixing techniques.

| Component | Percent by Weight of Composition |
|---|---|
| Polypropylene Glycol 15 Stearyl Ether | 15.00 |
| Sorbitan Oleate | 2.00 |
| Octyl Methoxy Cinnamate | 7.50 |
| Myristyl Lysophosphatidic Acid | 0.50 |
| Propyl Paraben | 0.15 |
| Butylated Hydroxy Toluene | 0.05 |
| Cyclomethicone | 20.00 |
| Sesame Oil | 5.00 |
| Mineral Oil (Blandol) | 49.80 |

This composition is useful for topical application to inhibit damage caused by acute or chronic UV exposure. Use of an amount of the composition is sufficient to deposit about 0.1 mg/cm$^2$ of the anti-wrinkle agent to the skin is appropriate.

EXAMPLE VIII

| Component | Percent by Weight of Composition |
|---|---|
| Deionized Water | 97.63 |
| Oleyl Lysophosphatidic Acid | 2.00 |
| EDTA | 0.37 |

This composition is useful for topical application to regulate skin wrinkles. Use of an amount of the composition to deposit about 0.5 mg/cm$^2$ of the anti-wrinkle agent to the skin is appropriate.

While particular embodiments of the subject invention have been described, it sill be obvious to those skilled in the art that various changes and modifications of the subject invention can be made without departing from the spirit and scope of the invention. It is intended to cover, in the appended claims, all such modifications that are within the scope of the invention.

What is claimed is:

1. A method of preventing, retarding, arresting or reversing the process of wrinkle formation in mammalian skin comprising topically applying to the skin of a mammal a composition comprising a safe and effective amount of a lysophosphatidic acid compound having the structure:

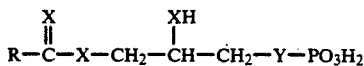

or a cyclic derivative thereof having the structure:

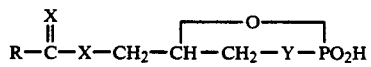

or a pharmaceutically acceptable salt thereof, wherein —R is unsubstituted or substituted with a substituent selected from the group consisting of halogen, hydroxy, phenyl, amino and acylamino, saturated or unsaturated, straight or branched chain alkyl having from 12 to about 23 carbon atoms; each —X— is independently —O— or —S—; and —Y— is —O— or —CH$_2$—.

2. The method of claim 1 wherein —R is unsubstituted or substituted with hydroxy or halogen.

3. The method of claim 2 wherein —X— —O—.

4. The method of claim 3 wherein the compound has the structure.

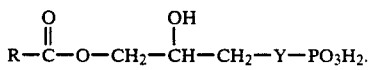

5. The method of claim 4 wherein —Y— is —O—.

6. The method of claim 5 wherein —R is unsubstituted.

7. The method of claim 6 wherein —R is straight-chain and is saturated or unsaturated with one double bond.

8. The method of claim 7 wherein —R has from bout 13 to 17 carbon atoms.

9. The method of claim 8 wherein RC(O)O— is selected from the group consisting of oleyl, palmityl and myristyl.

10. The method of claim 9 wherein RC(O)O— is myristyl.

11. The method of claim 1 wherein the amount of the lysophosphatidic acid compound applied to the skin is from about 0.01 mg to about 1 mg per cm$_2$ skin.

12. The method of claim 6 wherein the amount of the lysophosphatidic acid compound applied to the skin is from about 0.01 mg to about 1 mg per cm$_2$ skin.

13. The method of claim 8 wherein the amount of the lysophosphatidic acid compound applied to the skin is from about 0.01 mg to about 1 mg per cm$_2$ skin.

14. The method of claim 9 wherein the amount of the lysophosphatidic acid compound applied to the skin is from about 0.01 mg to about 1 mg per cm$_2$ skin.

15. A composition for topical application for preventing, retarding, arresting or reversing the process of wrinkle formation in mammalian skin comprising:

(a) a safe and effective amount of a lysophosphatidic acid compound having the structure:

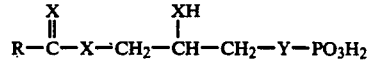

or a cyclic derivative thereof having the structure:

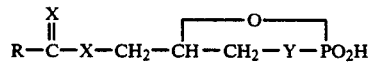

or a pharmaceutically acceptable salt thereof, wherein —R is unsubstituted or substituted with a substituent selected from the group consisting of halogen, hydroxy, phenyl, amino and acylamino, saturated or unsaturated, straight or branched chain alkyl having from 12 to about 23 carbon atoms; each —X— is independently —O— or —S—; and —Y— is —O— or —CH$_2$—.

(b) a safe and effective amount of a chelating agent capable of forming a complex with a metal ion so that the ion cannot participate in or catalyze chemical reactions; and (c) a safe and effective amount of a topical carrier.

16. The composition of claim 15 wherein the compound has the structure:

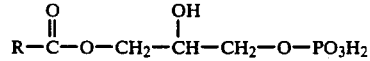

wherein —R has from 13 to 17 carbon atoms, is straight-chain, is unsubstituted, and is saturated or has one double bond.

* * * * *